United States Patent [19]

Finitzo et al.

[11] Patent Number: 5,003,986

[45] Date of Patent: Apr. 2, 1991

[54] HIERARCHIAL ANALYSIS FOR PROCESSING BRAIN STEM SIGNALS TO DEFINE A PROMINENT WAVE

[75] Inventors: Terese Finitzo, Dallas, Tex.; Kenneth D. Pool, Jr., 3001 Coronado, Irving, Tex. 75062

[73] Assignees: Kenneth D. Pool, Jr.; Electrophysiology Laboratories of Dallas, Inc., both of Dallas, Tex. ; a part interest

[21] Appl. No.: 272,714

[22] Filed: Nov. 17, 1988

[51] Int. Cl.$^5$ ............................................. A61B 5/04
[52] U.S. Cl. ................................. 128/731; 364/413.05
[58] Field of Search .............................. 128/731–733, 128/680; 364/413.02–413.05

[56] References Cited

U.S. PATENT DOCUMENTS

| | | | |
|---|---|---|---|
| 3,892,227 | 7/1975 | Coursin et al. | 128/731 |
| 4,171,696 | 10/1979 | John | 128/731 |
| 4,188,956 | 2/1980 | John | 128/731 |
| 4,201,224 | 5/1980 | John | 128/731 |
| 4,214,594 | 7/1980 | Sato et al. | 128/731 |
| 4,215,697 | 8/1980 | Demetrescu | 128/731 |
| 4,216,781 | 8/1980 | John | 128/731 |
| 4,219,028 | 8/1980 | Lencioni, Jr. | 128/731 |
| 4,254,779 | 3/1981 | Miyata et al. | 128/731 |
| 4,275,744 | 6/1981 | Thornton et al. | 128/731 |
| 4,279,258 | 7/1981 | John | 128/731 |
| 4,323,079 | 4/1982 | Demetrescu | 128/731 |
| 4,407,299 | 10/1983 | Culver | 128/731 |
| 4,408,616 | 10/1983 | Duffy et al. | 128/731 |
| 4,411,273 | 10/1983 | John | 128/731 |
| 4,417,591 | 11/1983 | Culver | 128/731 |
| 4,417,592 | 11/1983 | John | 128/731 |
| 4,421,122 | 12/1983 | Duffy | 128/731 |
| 4,545,388 | 10/1985 | John | 128/731 |
| 4,557,270 | 12/1985 | John | 128/731 |
| 4,579,125 | 4/1986 | Strobl et al. | 128/731 |
| 4,583,190 | 4/1986 | Salb | 364/413.05 |
| 4,603,703 | 8/1986 | McGill et al. | 364/413.05 |
| 4,610,259 | 9/1986 | Cohen et al. | 128/731 |
| 4,611,284 | 9/1986 | McGill et al. | 128/733 X |
| 4,649,482 | 3/1987 | Raviv et al. | 364/413.05 |
| 4,678,519 | 7/1987 | Yamaguchi | 128/680 |
| 4,697,598 | 10/1987 | Bernard et al. | 128/731 |
| 4,705,049 | 11/1987 | John | 128/731 |
| 4,736,307 | 4/1988 | Salb | 364/413.05 |
| 4,736,751 | 4/1988 | Gevins et al. | 128/731 |
| 4,739,772 | 4/1988 | Hokanson et al. | 128/731 |
| 4,744,029 | 5/1988 | Raviv et al. | 364/413.05 |
| 4,840,181 | 6/1989 | Yamaguchi | 128/681 X |
| 4,844,086 | 7/1989 | Duffy | 128/731 |

Primary Examiner—Francis Jaworski
Attorney, Agent, or Firm—Richards, Medlock & Andrews

[57] ABSTRACT

A signal waveform analyzation technique which filters digital data to define primary peaks. Unfiltered data of the primary peaks is then employed to define secondary peaks associated with the primary peak. Amplitude and time characteristic data associated with the secondary peaks is then employed to determine reproducibility of secondary peaks between the pair of traces. A hierarchial analysis is utilized to further analyze the reproducible pairs of secondary peaks to identify a prominent wave. Depending on the success of a first pass, the digital data is filtered with a different bandpass, whereupon the analyzation steps are again repeated in an attempt to identify a prominent wave.

36 Claims, 20 Drawing Sheets

FIG. 8a

```
1.      INTEGER CUR,BP,A1(1024),A2(1024),A5(1024),A6(1024),FIN
2.      INTEGER EP,FIRST,LAST,NFP,DTSZ,NDX,I,J,K,TEMP(200)
3.      INTEGER MAX,MIN,POP,TOT,ALIM,CUR2,PNP,NW1,NW2,TEST
4.      INTEGER PP1(50),FP1(50),PN1(50),PT1(50),TP1(50),TA1(50)
5.      INTEGER PP2(50),FP2(50),PN2(50),PT2(50),TP2(50),TA2(50)
6.      INTEGER SEN,NSWP,SWTM,NPPOST,UITV,TRMD,TR,LD(20)
7.      INTEGER NRW,RW1(20),RW2(20),V,V1,V2,LA1,LA2,SA1,SA2
8.      INTEGER SFP1,SFP2,LFP1,LFP2
9.      INTEGER DUM1,DUM2,DUM3,DUM4,DUM5,DUM6,DUM7,DUM8,ITD
10.     REAL RA1(50),RA2(50),RAT,X,Y,DWELL
11.     CHARACTER *30 DUMMY,CR,CONC,C1,C2,TERM
12.     CHARACTER *80 C
13.     CHARACTER *1 CHAN(3)
14.     CHARACTER *4 DEVICE(2)

15.     CHAN(1)='1'
16.     CHAN(2)='2'
17.     CHAN(3)='0'
18.     DEVICE(1)='AUD '
19.     DEVICE(2)='MSA '

20.     CALL PTHCMD('SCROLL:C\')
21.     TR=100
22.     NDX = TR*16
23.     DO 1111 TR=1,NDX,16
24.
25.     V1=0
26.     V2=0
27.     CALL PTHCMD('SCROLL:C\')
28.     CALL ITOC(TR,C1)
29.     C = CONC('RTV[\',C1,'] ETST.DAT-D0 A1-B8\')
30.     CALL PTHCMD(C)
31.     CALL ITOC(V1,C1)
32.     CALL ITOC(V2,C2)
33.     C = CONC('CSR1 A1=\',C1)
34.     CALL PTHCMD(C)
35.     C = CONC('CSR1 A2=\',C2)
36.     CALL PTHCMD(C)
37.     CALL PTHCMD('DSP A1 A2\')
```

FIG. 8b

```
38.        CALL GETDATA('EPOCH.A1\',10,SEN)
39.        CALL GETDATA('EPOCH.A1\',9,NSWP)
40.        CALL GETDATA('EPOCH.A1\',5,DTSZ)
41.        CALL GETDATA('EPOCH.A1\',6,SWTM)
42.        CALL GETDATA('EPOCH.A1\',17,NPPOST)
43.        CALL GETDATA('EPOCH.A1\',16,TRMD)

44.        CALL GETDATA('EPOCH.A2\',10,DUM1)
45.        CALL GETDATA('EPOCH.A2\',5,DUM2)
46.        CALL GETDATA('EPOCH.A2\',6,DUM3)
47.        CALL GETDATA('EPOCH.A2\',17,DUM4)
48.        CALL GETDATA('EPOCH.A2\',16,DUM5)
49.
50.        IF (SEN .NE. DUM1) THEN
51.           GOTO 998
52.        ENDIF

53.        IF (DTSZ .NE. DUM2) THEN
54.           GOTO 998
55.        ENDIF
56.        IF (SWTM .NE. DUM3) THEN
57.           GOTO 998
58.        ENDIF
59.        IF (NPPOST .NE. DUM4) THEN
60.           GOTO 998
61.        ENDIF
62.        IF (TRMD .NE. DUM5) THEN
63.           GOTO 998
64.        ENDIF

65.        IF (TRMD .EQ. 4) THEN
66.           NPPOST=0
67.        ENDIF
68.        IF ((TRMD .EQ. 2) .AND. (NPPOST .GT. 0)) THEN
69.           NPPOST=DTSZ-NPPOST
70.        ENDIF 71.
72.        DWELL = ((REAL(SWTM)*128.0)/(REAL(DTSZ)*125.0))

73.        BP = INT(5.2/DWELL) + NPPOST
74.        EP = INT(10.2/DWELL) + NPPOST
75.        UITV = NINT(0.25/DWELL)
76.        NFP = NINT(0.9/DWELL)
77.        IF (EP .GE. (DTSZ-NFP)) THEN
78.           EP=DTSZ-NFP
```

FIG. 8c

```
79.            ENDIF
80.            ALIM = NINT((128.0*REAL(NSWP)*75.0)/(500.0*REAL(SEN)))

81.            FIN=1
82.     10     CONTINUE
83.            NW1=0
84.            NW2=0

85.            CALL GETBLK('A1\',0,A1,DTSZ)
86.            CALL GETBLK('A2\',0,A2,DTSZ)
87.            CALL GETBLK('A5\',0,A5,DTSZ)
88.            CALL GETBLK('A6\',0,A6,DTSZ)

89.            CUR=BP
90.            GOTO 510
91.     500    IF (A5(CUR) .LE. 0) THEN
92.              CUR=CUR+1
93.              IF (CUR .LE. EP) THEN
94.                GOTO 500
95.              ELSE
96.                GOTO 900
97.              ENDIF
98.            ENDIF
99.
100.    510    IF (A5(CUR) .GT. 0) THEN
101.             CUR=CUR+1
102.             IF (CUR .LE. EP) THEN
103.               GOTO 510
104.             ELSE
105.               GOTO 900
106.             ENDIF
107.           ENDIF
108.           FIRST=CUR-1
109.           CUR=CUR+1
110.
111.    520    IF ((A5(CUR) .LT. 10) .AND. (CUR .LT. (FIRST+NFP))) THEN
112.             CUR=CUR+1
113.             IF (CUR .LE. DTSZ) THEN
114.               GOTO 520
115.             ELSE
116.               GOTO 900
117.             ENDIF
118.           ENDIF
119.           LAST=CUR-1
120.    525    IF (A5(CUR) .LT. 10) THEN
121.             CUR=CUR+1
122.             IF (CUR .LE. DTSZ) THEN
123.               GOTO 525
124.             ELSE
125.               GOTO 527
126.             ENDIF
```

FIG. 8d

```
127.            ENDIF
128.    527     CONTINUE
129.
130.            TEST=CUR-1
131.            NDX=0
132.            DO 530 I=FIRST,LAST
133.              IF (((A1(I)-A1(I-2)) .GT. -30) .OR. (I .EQ. FIRST)) THEN
134.                NDX=NDX+1
135.                TEMP(NDX)=I
136.              ENDIF
137.    530     CONTINUE
138.            MAX=-99999
139.            DO 540 I=FIRST,LAST
140.              IF (A1(I) .GT. MAX) THEN
141.                MAX=A1(I)
142.              ENDIF
143.    540     CONTINUE
144.            POP=0
145.            MIN=A1(LAST)
146.            TOT=MAX-MIN
147.            IF (TOT .GE. ALIM) THEN
148.              MIN = A1(TEST)
149.              TOT = MAX-MIN
150.              TOT = INT(0.55 * REAL(TOT))
151.              DO 550 I=1,NDX
152.                DUM6=A1(TEMP(I))-MIN
153.                IF ((A1(TEMP(I))-MIN) .GT. TOT) THEN
154.                  POP= TEMP(I)
155.                  CUR2=POP
156.    560         IF ((A5(CUR2) .GE. (-10)) .AND. (CUR2 .GT. 1)) THEN
157.                  CUR2=CUR2-1
158.                  GOTO 560
159.                ENDIF
160.                PNP=CUR2
161.                NW1=NW1+1
162.                PP1(NW1)=POP
163.                FP1(NW1)=TEST
164.                PN1(NW1)=PNP
165.                PT1(NW1)=A1(POP)-A1(TEST)
166.                TP1(NW1)=A1(POP)-A1(PNP)
167.                IF (TP1(NW1) .LT. 0) THEN
168.                  TP1(NW1)=0
169.                ENDIF
170.                TA1(NW1)=TP1(NW1)+PT1(NW1)
171.                RA1(NW1)= REAL(TP1(NW1))/REAL(PT1(NW1))
172.              ENDIF
173.    550     CONTINUE
174.            ENDIF 175.    590     IF (CUR .LT. EP) THEN
176.              GOTO 500
177.            ENDIF
```

FIG. 8e

```
178.  900    IF (NW1 .LE. 0) THEN
179.            GOTO 910
180.         ENDIF
181.         CUR=BP
182.         CALL GETDATA('EPOCH.A2\',10,SEN)
183.         CALL GETDATA('EPOCH.A2\',9,NSWP)
184.         ALIM = NINT((128.0*REAL(NSWP)*75.0)/(500.0*REAL(SEN)))
185.         GOTO 610
186.
187.
188.
189.  600    IF (A6(CUR) .LE. 0) THEN
190.            CUR=CUR+1
191.            IF (CUR .LE. EP) THEN
192.               GOTO 600
193.            ELSE
194.               GOTO 910
195.            ENDIF
196.         ENDIF
197.
198.  610    IF (A6(CUR) .GT. 0) THEN
199.            CUR=CUR+1
200.            IF (CUR .LE. EP) THEN
201.               GOTO 610
202.            ELSE
203.               GOTO 910
204.            ENDIF
205.         ENDIF
206.         FIRST=CUR-1
207.         CUR=CUR+1
208.
209.  620    IF ((A6(CUR) .LT. 10) .AND. (CUR .LT. (FIRST+NFP))) THEN
210.            CUR=CUR+1
211.            IF (CUR .LE. DTSZ) THEN
212.               GOTO 620
213.            ELSE
214.               GOTO 910
215.            ENDIF
216.         ENDIF
217.         LAST=CUR-1
218.  626    IF (A6(CUR) .LT. 10.) THEN
219.            CUR=CUR+1
220.            IF (CUR .LE. DTSZ) THEN
221.               GOTO 626
222.            ELSE
223.               GOTO 627
224.            ENDIF
225.         ENDIF
226.  627    CONTINUE
227.         TEST=CUR-1
228.         NDX=0
229.         DO 630 I=FIRST,LAST
230.            IF (((A2(I) - A2(I-2)) .GT. -30) .OR. (I .EQ. FIRST)) THEN
231.               NDX=NDX+1
232.               TEMP(NDX)=I
```

FIG. 8f

```
233.           ENDIF
234.    630    CONTINUE
235.           MAX=-99999
236.           DO 640 I=FIRST,LAST
237.             IF (A2(I) .GT. MAX) THEN
238.               MAX=A2(I)
239.             ENDIF
240.    640    CONTINUE
241.           POP=0
242.           MIN=A2(LAST)
243.           TOT=MAX-MIN
244.           IF (TOT .GE. ALIM) THEN
245.             MIN = A2(TEST)
246.             TOT = MAX-MIN
247.             TOT = INT(0.55 * REAL(TOT))
248.             DO 650 I=1,NDX
249.               DUM6=A2(TEMP(I))-MIN
250.               IF ((A2(TEMP(I))-MIN) .GT. TOT) THEN
251.                 POP= TEMP(I)
252.                 CUR2=POP
253.    660        IF ((A6(CUR2) .GE. (-10)) .AND. (CUR2 .GT. 1)) THEN
254.                 CUR2=CUR2-1
255.                 GOTO 660
256.               ENDIF
257.               PNP=CUR2
258.               NW2=NW2+1
259.               PP2(NW2)=POP
260.               FP2(NW2)=TEST
261.               PN2(NW2)=PNP
262.               PT2(NW2)=A2(POP)-A2(TEST)
263.               TP2(NW2)=A2(POP)-A2(PNP)
264.               IF (TP2(NW2) .LT. 0) THEN
265.                 TP2(NW2) = 0
266.               ENDIF
267.               TA2(NW2)=TP2(NW2)+PT2(NW2)
268.               RA2(NW2)= REAL(TP2(NW2))/REAL(PT2(NW2))
269.             ENDIF
270.    650    CONTINUE
271.           ENDIF 272.    690    IF (CUR .LT. EP) THEN
273.             GOTO 600
274.           ENDIF 275.    910    CONTINUE
```

FIG. 8g

```
276.            V=0
277.            NRW=0
278.            IF ((NW1 .EQ. 0) .OR. (NW2 .EQ. 0)) THEN
279.              V=0

280.              CR='NW1 OR NW2 = 0'
281.              GOTO 800
282.            ENDIF
283.            DO 700 I=1,NW1
284.              DO 710 J=1,NW2
285.                K=PP1(I)-PP2(J)
286.                IF ((K .LE. UITV) .AND. (K .GE. (-1*UITV))) THEN
287.                  NRW=NRW+1
288.                  RW1(NRW)=I
289.                  RW2(NRW)=J
290.                  LD(NRW)=K
291.                ENDIF
292.    710       CONTINUE
293.    700     CONTINUE
294.            IF (NRW .LE. 0) THEN
295.              V=0
296.              CR='NRW = 0'
297.              GOTO 800
298.            ENDIF
299.            IF (NRW .EQ. 1) THEN
300.              V=NRW
301.              CR='NRW = 1'
302.              GOTO 800
303.            ENDIF
304.            CALL PTHCMD('SCROLL:C\')
305.            LA1=0
306.            LA2=0

307.            DO 730 I=1,NRW
308.              IF (PT1(RW1(I)) .GT. LA1) THEN
309.                LA1=PT1(RW1(I))
310.                LFP1=FP1(RW1(I))
311.              ENDIF
312.              IF (PT2(RW2(I)) .GT. LA2) THEN
313.                LA2=PT2(RW2(I))
314.                LFP2=FP2(RW2(I))
315.              ENDIF
316.    730     CONTINUE
317.            SA1=0
318.            SA2=0
319.            DO 735 I=1,NRW
320.              IF ((PT1(RW1(I)) .GT. SA1) .AND. (FP1(RW1(I)) .NE. LFP1)) THEN
321.                SA1=PT1(RW1(I))
322.                SFP1=FP1(RW1(I))
323.              ENDIF
324.              IF ((PT2(RW2(I)) .GT. SA2) .AND. (FP2(RW2(I)) .NE. LFP2)) THEN
325.                SA2=PT2(RW2(I))
326.                SFP2=FP2(RW2(I))
327.              ENDIF
328.    735     CONTINUE
```

FIG. 8h

```
329.          SA1=SA1*2
330.          SA2=SA2*2
331.          IF (LA1 .GE. SA1) THEN
332.           ITD=99999
333.           DO 737 I=1,NRW
334.            IF (FP1(RW1(I)) .EQ. LFP1) THEN
335.             IF (LD(I) .LT. ITD) THEN
336.              V=I
337.             ELSE IF (LD(I) .EQ. ITD) THEN
338.              IF (PP1(RW1(I)) .LT. PP1(V)) THEN
339.               V=I
340.              ENDIF
341.             ENDIF
342.            ENDIF
343.  737     CONTINUE
344.          CR='LA1>SA1'
345.          GOTO 800
346.         ENDIF
347.         IF (LA2 .GE. SA2) THEN
348.          ITD=99999
349.          DO 738 I=1,NRW
350.           IF (FP2(RW2(I)) .EQ. LFP2) THEN
351.            IF (LD(I) .LT. ITD) THEN
352.             V=I
353.            ELSE IF (LD(I) .EQ. ITD) THEN
354.             IF (PP2(RW2(I)) .LT. PP2(V)) THEN
355.              V=I
356.             ENDIF
357.            ENDIF
358.           ENDIF
359.  738    CONTINUE
360.         CR='LA2>=SA2'
361.         GOTO 800
362.         ENDIF

363.         ITD=99999
364.         DO 740 I=1,NRW
365.          IF ((FP1(RW1(I)) .EQ. LFP1) .AND. (FP2(RW2(I)) .EQ. LFP2)) THEN
366.           IF (LD(I) .LT. ITD) THEN
367.            V=I
368.           ELSE IF (LD(I) .EQ. ITD) THEN
369.            IF (PP1(RW1(I)) .LT. PP1(V)) THEN
370.             V=I
371.            ELSE IF (PP1(RW1(I)) .EQ. PP1(V)) THEN
372.             IF (PP2(RW2(I)) .LT. PP2(V)) THEN
373.              V=I
374.             ENDIF
375.            ENDIF
376.           ENDIF
377.          ENDIF
378.  740   CONTINUE
379.        IF (ITD .LT. 99999) THEN
380.         CR='LFP1=LFP2'
381.         GOTO 800
382.        ENDIF
```

FIG. 8i

```
383.        DO 745 I=1,NRW
384.          IF ((FP1(RW1(I)) .EQ. LFP1) .AND. (FP2(RW2(I)) .EQ. SFP2)) THEN
385.            IF (LD(I) .LT. ITD) THEN
386.              V=I
387.            ELSE IF (LD(I) .EQ. ITD) THEN
388.              IF (PP1(RW1(I)) .LT. PP1(V)) THEN
389.                V=I
390.              ELSE IF (PP1(RW1(I)) .EQ. PP1(V)) THEN
391.                IF (PP2(RW2(I)) .LT. PP2(V)) THEN
392.                  V=I
393.                ENDIF
394.              ENDIF
395.            ENDIF
396.          ENDIF
397.  745   CONTINUE
398.        IF (ITD .LT. 99999) THEN
399.          CR='LFP1=SFP2'
400.          GOTO 800
401.        ENDIF

402.        DO 750 I=1,NRW
403.          IF ((FP1(RW1(I)) .EQ. SFP1) .AND. (FP2(RW2(I)) .EQ. LFP2)) THEN
404.            IF (LD(I) .LT. ITD) THEN
405.              V=I
406.            ELSE IF (LD(I) .EQ. ITD) THEN
407.              IF (PP1(RW1(I)) .LT. PP1(V)) THEN
408.                V=I
409.              ELSE IF (PP1(RW1(I)) .EQ. PP1(V)) THEN
410.                IF (PP2(RW2(I)) .LT. PP2(V)) THEN
411.                  V=I
412.                ENDIF
413.              ENDIF
414.            ENDIF
415.          ENDIF
416.  750   CONTINUE
417.        IF (ITD .LT. 99999) THEN
418.          CR='SFP1=LFP2'
419.          GOTO 800
420.        ENDIF

421.        DO 760 I=1,NRW
422.          IF ((FP1(RW1(I)) .EQ. SFP1) .AND. (FP2(RW2(I)) .EQ. SFP2)) THEN
423.            IF (LD(I) .LT. ITD) THEN
424.              V=I
425.            ELSE IF (LD(I) .EQ. ITD) THEN
426.              IF (PP1(RW1(I)) .LT. PP1(V)) THEN
427.                V=I
```

FIG. 8j

```
428.            ELSE IF (PP1(RW1(I)) .EQ. PP1(V)) THEN
429.              IF (PP2(RW2(I)) .LT. PP2(V)) THEN
430.                V=I
431.              ENDIF
432.            ENDIF
433.          ENDIF
434.        ENDIF
435.  760   CONTINUE
436.        IF (ITD .LT. 99999) THEN
437.          CR='SFP1=SFP2'
438.          GOTO 800
439.        ENDIF

440.        V=1
441.        X=RA1(RW1(1))+RA2(RW2(1))
442.        DO 725 I=2,NRW
443.          RAT=RA1(RW1(I))+RA2(RW2(I))
444.          IF (RAT .LT. X) THEN
445.            X=RAT
446.            V=I
447.          ENDIF
448.  725   CONTINUE
449.        CR='RAT'

450.  800   IF ((V .EQ. 0) .AND. (FIN .LT. 6)) THEN
451.          CALL PTHCMD('ZAP A3-A6\')
452.          GOTO(802,803,804,805,806),FIN 453.  802   CALL PTHCMD('MOVE A7 A8 A3 A4\')
454.        GOTO 810

455.  803   CALL PTHCMD('MOVE B1 B2 A3 A4\')
456.        GOTO 810

457.  804   CALL PTHCMD('MOVE B3 B4 A3 A4\')
458.        GOTO 810

459.  805   CALL PTHCMD('MOVE B5 B6 A3 A4\')
460.        GOTO 810

461.  806   CALL PTHCMD('MOVE B7 B8 A3 A4\')
462.        GOTO 810

463.  810   CALL PTHCMD('DIF A3 A5\')
464.        CALL PTHCMD('DIF A4 A6\')
465.        FIN=FIN+1
466.        GOTO 10
```

FIG. 8k

```
467.            ENDIF

468.            DUM5=1+(TR/16)
469.            IF (V .EQ. 0) THEN
470.              V1 = 0
471.              V2 = 0
472.              CALL PTHCMD('SCROLL:C\')
473.            ELSE
474.              CALL PTHCMD('SCROLL:C\')
475.              V1=PP1(RW1(V))-1
476.              V2=PP2(RW2(V))-1
477.            ENDIF
478.            CALL ITOC(V1,C1)
479.            CALL ITOC(V2,C2)
480.            C = CONC('CSR1 A1=\',C1)
481.            CALL PTHCMD(C)
482.            C = CONC('CSR1 A2=\',C2)
483.            CALL PTHCMD(C)
484.            GOTO 999

485.      998   CALL PTHCMD('SCROLL:C\')
486.            GOTO 1999

```
490.         DO 2200 J=1,2
491.           DO 2210 K=1,3
492.             I = IPARMS('A1',DEVICE(J),CHAN(K),'MODE ',VALUE)
493.             IF (I .GE. 0) THEN
494.               IF ((VALUE .GT. 0.0) .AND. (VALUE .LT. 4.0)) THEN
495.                 GOTO 2220
496.               ENDIF
497.             ENDIF
498.  2210   CONTINUE
499.  2200   CONTINUE
500.         GOTO 1999

501.  2220   I = IPARMS('A1',DEVICE(J),CHAN(K),'LEVEL',VALUE)
502.         IF (VALUE .LT. 60.0) THEN
503.           GOTO 1999
504.         ENDIF
505.
506.

507.  1999   CONTINUE
508.  1993   PRINT*,'INTENSITY WAS ',VALUE
509.         CALL PTHCMD('DSP A1 A2\')

510.         CALL PTHCMD('LOG A1 A2 V7ANAL.DAT-D0\')
511.  1111   CONTINUE 512.  1112   CONTINUE

513.         END
```

FIG. 8m

COMPILATION COMPLETED
NO ERRORS FOUND

HIERARCHIAL ANALYSIS FOR PROCESSING BRAIN STEM SIGNALS TO DEFINE A PROMINENT WAVE

TECHNICAL FIELD OF THE INVENTION

This invention relates in general to waveform analysis, and particularly to a computer-automated identification program which is an on-line procedure for analyzing waveform response morphology characteristics to determine the presence or absence of a prominent wave and identify the same.

BACKGROUND OF THE INVENTION

In many fields, such as in the medical sciences, an experienced person is required to analyze brain waveforms for certain characteristics and provide corresponding conclusions. An experienced analyzer often uses a set of decision making criteria when deciding whether or not a brain waveform exhibits a particular characteristic. The skilled person many times analyzes waveform slope, latency, amplitude, intertrial reproducibility, and other specific morphologic patterns. Various apparatus and computer programs are available to aid the waveform analyzer with such analysis.

One example of waveform analysis of electrical brain signals is when a clinician tests the hearing of a patient. In order to test the hearing of young children or infants, or of adults who cannot respond to an audiologist testing the hearing response, a clinician can measure the auditory brain stem response (ABR) of the patient. By analyzing a visual display of the waveform of the auditory brain stem response, a clinician can often determine from the characteristics of the waveform whether the patient has a hearing problem. Other physiological and brain related dysfunctions can also be detected, diagnosed or monitored by visually analyzing the waveform display.

An auditory brain stem response of a patient is obtained by placing electrodes at the vertex or crown of the head and behind the left and right ear of the patient. A click generator is employed to produce a clicking sound which is coupled to the patient's ears. The electrical signals generated by the brain and received by the electrodes are utilized to provide a visual display of the brain activity in response to the auditory stimulus. The clinician can then analyze the ABR waveform in order to determined whether there was any conscious or subconscious response to the audio clicking stimulus. In analyzing an ABR waveform and deciding whether the waveform contains a pattern which indicates a response to the audio stimulus, the experienced clinician carefully examines all the characteristics of the waveform to determine the presence or absence of waves well defined in this area, such as Waves I, II, III, IV and V. The presence or absence of each such wave signifies the ability of a person's brain to assimilate input audio stimulus and react accordingly.

Various apparatus and computer programs have been developed in an attempt to simplify brain waveform analysis. Such equipment is intended to provide results which replace the subjective decisions of the clinician, and thereby save the clinician from the time consuming and often strenuous task of brain wave analysis. Typically, such apparatus and computer programs are adapted to detect brain wave peaks which exceed a certain thresholds to determine whether the waveform indicates a certain response. Other computerized equipment is available for comparing measured brain waveforms with normal brain waveforms to determine whether an abnormality exists.

U.S. Pat. No. 4,275,744, by Thorton et al., and U.S. Pat. No. 4,545,388, by John, provide two examples of prior art for analyzing brain waves. In the Thorton et al. patent, audio frequency pulses are applied to the ear of the person being tested. Each audio stimulus is realized as a characteristic response in the form of an electroencephalographic (EEG) waveform produced by the subject. The EEG signal is then transmitted through a signal conditioner and then applied to a signal sampling device which samples the signal for responses at predetermined times. The predetermined times are selected by looking at the times that such a response occurs in an exemplary waveform. However, the operator then must determine the ratio of the number of pulses to the number of trial pulses over a selected period of time to provide a measure of the likelihood that a response is being evoked in a subject by the auditory signals. According to the teachings of the noted patent, the apparatus does not analyze the waveform and make decisions, rather the apparatus supplies the operator with specific data and the operator must then determine whether a response is being evoked in a patient by the auditory signals.

The John patent describes a technique for monitoring the state of a patient's brain during a medical procedure relative to a self-norm established at an earlier time. The self-norm is formed by electrical measurements taken of brain functions which are selected for medical relevance to the particular medical procedure. During the medical procedure, the same brain functions are electrically measured. Each new set of measurements is tested for statistically and medically significant changes from the self-norm and, if a test shows such a change, an indication is produced. The indication shows not only that a change has occurred, but also the ascribed medical significance of the change itself and the persistence of a change. Obviously, one major drawback to the technique is that if emergency medical procedures are necessary, it is unlikely that self-norm measurements are also available. Furthermore, although the method and apparatus can detect changes from the self-norm, the method and apparatus does not indicate whether the self-norm is in fact normal.

From the foregoing, it can be seen that a need exists for an on-line procedure which mathematically analyzes waveform morphology characteristics and which emulates the analysis of the experienced waveform analyzer in making particular determinations regarding certain waveform responses. Another need exists for an automatic waveform analysis technique which receives brain waveform data, carries out an analysis according to a hierarchy or predetermined criteria, and provides a positive visual identification of the desired wave if such criteria is satisfied.

SUMMARY OF THE INVENTION

In accordance with the present invention, the disclosed waveform analyzing method and technique substantially reduce or eliminate the disadvantages and the shortcomings associated with the prior art techniques. According to the invention, an on-line software program is employed with computerized waveform processing equipment for analyzing electrical signal waveforms and for identifying particular waves in accordance with predetermined criteria arranged in a hierarchial decision making process.

In accordance with the preferred embodiment of the invention, brain wave signals are digitized and stored for analysis, either on-line, or for subsequent analyzation, to identify predominant waves, such as Wave V produced in audio evoked brain stem responses. According to the technique of the invention, first and second related signal waveform traces are converted to digital signals and processed to determine primary peaks and associated troughs. If initial primary peaks and associated troughs are not found, the digital signals are filtered, whereupon the analyzation is repeated. The digital data of the primary peaks of both traces is further analyzed to define secondary peaks and associated valleys. Once the secondary peaks and associate valleys of the digital signals have been defined, the digital waveform data is utilized to characterize amplitude characteristics of each of the secondary peaks. The secondary peaks of each waveform trace are then further analyzed to determine reproducibility therebetween by ascertaining a time or latency relationship between pairs of secondary peaks of the respective first and second waveform traces.

A hierarchial analysis is then carried out for the defined reproducible pairs of secondary peaks to define whether or not a prominent wave exists, and to define a point on the prominent wave which particularly characterizes the wave. A program controlled processor employing the program displays both waveform traces and the selected point on the prominent wave which particularly identifies the latency of the wave. The hierarchial analysis includes a first pass which utilizes time and amplitude characteristics of the secondary peaks, if no prominent wave is definable, the analysis is repeated, but using the digital signals filtered with a narrower bandpass. The technique is carried out repetitively with a predefined number of filter bandpasses, whereupon, if a prominent wave does not exist, the waveform is displayed without identification thereof.

BRIEF DESCRIPTION OF THE DRAWINGS

Further features and advantages will become apparent from the following and more particular description of the preferred embodiment of the invention, as illustrated in the accompanying drawings in which like reference characters generally refer to the same elements or functions throughout the views, and in which:

FIGS. 8a-8m are a number of pages of a software program according to the preferred embodiment of the invention.

DETAILED DESCRIPTION

While the following description is directed to a particular application of the invention, it is to be understood that the principles and concepts of the invention can be employed in many other applications, whether or not medically related. It may be advantageous to use one or more of the hierarchial waveform analysis steps described herein to identify certain characteristics of other types of waveforms.

Figure 1:
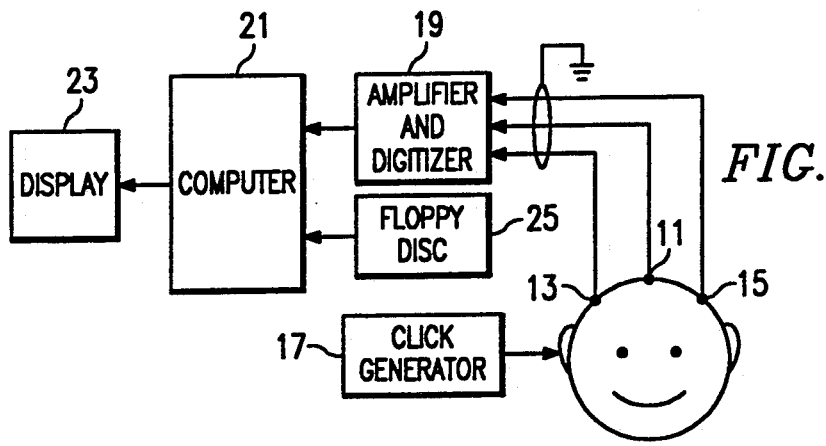
FIG. 1 is a simplified diagram of the equipment and environment in which the invention can be advantageously practiced.

FIG. 1 is a generalized schematic diagram illustrating the instrumentation employed for utilizing the invention in measuring auditory brain stem responses. Three electrodes 11, 13, 15 of conventional design are placed on the surface of a patient's scalp. One electrode 11 is placed at the vertex or crown of the head, while another electrode 13 is placed on a mastoid location of the patient's right ear. A third electrode 15 is placed on the mastoid location of the patient's left ear. The auditory brain stem response is measured as a differential electrical signal between the electrode 11 at the vertex and either the electrode 13 of the right ear, or the electrode 15 of the left ear. A positive response indicates that the brain and brain stem are functioning properly to assimilate the audio signal coupled to the right ear. To test the hearing of the left ear, an auditory brain stem response is obtained between the electrode 11 at the vertex and the electrode 15 on the mastoid of the left ear. While signal waveforms are obtained in the manner noted in FIG. 1 for analyzing brain wave signals, other signal acquisition techniques may be employed to provide data for analyzation according to the invention.

After the electrodes are attached, an auditory stimulus is applied to the patient's ears. The auditory stimulus is generated by a click generator which transmits a number of click sounds, via a pair of earphones (not shown), to the ears being tested. The intensity and the frequency of the click sounds can be of a level conventionally utilized by audiologists. A large number of the clicks (for example, 2,000) are transmitted to the ear being tested. A corresponding number of brain wave responses are generated by the patient's brain and are collected by the electrodes, recorded by the computer equipment, and averaged together to obtain a single waveform. The averaging of the large number of responses removes the inherent random brain activity noise and more clearly defines the true auditory brain wave response to the audio stimulus.

The resulting analog waveform signals are coupled to the differential input of an amplifier and digitizer 19. The sampling frequency of the equipment 19 can be selected to achieve a desired accuracy and resolution, but preferably may be in the order of 40 microseconds for analyzing brain waves. The amplifier 19 provides sufficient amplification of the very weak brain waves for efficient conversion to digital signals. This can be appreciated in view that typical electrical waves generated by the brain are generally less than a microvolt in amplitude. The digitized waveform is stored in a sequence of digital signals in the memory of a computer 21 either for on-line or subsequent analyzation. The results of the computerized analyzation can be displayed for further analysis by a clinician. A CRT display 23 is coupled to the computer 21 provides one medium for displaying the waveforms as analyzed by the computer 21. The results can also be displayed as a graphical or numerical printout, or plotted on a plotter. Many times, a patient is tested and the resulting waveforms are stored, for example on a computer floppy diskette 25, to be analyzed according to the invention at a later time.

The waveform analysis technique of the invention performs a hierarchial analysis of digital signals representative of a waveform to identify a prominent wave. In medical applications, the waveform analysis is applied to auditory brain stem response waveforms for defining a prominent wave which indicates the patient's degree of hearing ability. One important prominent wave is commonly known as "Wave V". The presence of a Wave V indicates to the clinician that the patient's aural organs has responded to the auditory click stimulus. Other waves, such as Waves I, II, III, and IV can be analyzed by the technique of the invention to yield indications also of hearing, as well as the physiological state of other organs of the human anatomy.

In general, the hierarchial analysis, described in detail below, involves analysis of certain criteria of brain stem waveforms occurring during a particular latency range or time period. As used herein, the term latency means a time period which starts at the application of the audio stimulus to the aural organs of the patient. The program first analyzes the raw gathered data of one waveform trace for a primary peak having a particular amplitude. If the waveform does not meet this amplitude criteria, the data signals of the waveform are filtered according to a particular bandpass, and again analyzed for a primary peak. The filtering and analyzing is repeated until a primary peak is found. If no such peak is found, this indicates that a particular response (Wave V) is not present.

Figure 2:
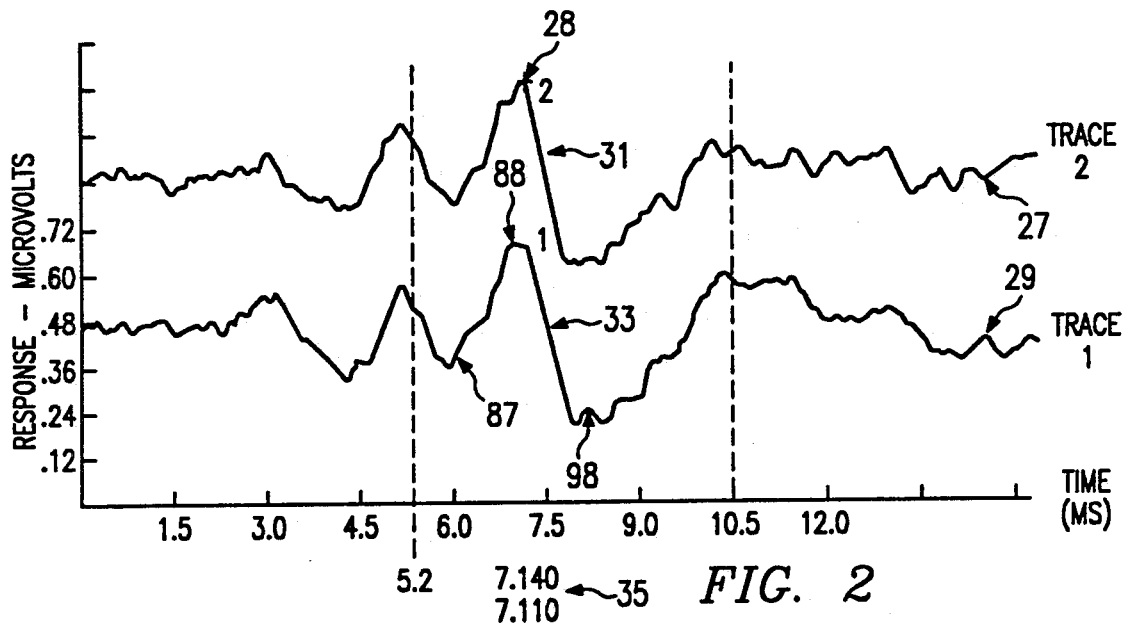
FIGS. 2 and 3 are waveform diagrams of brain stem waves of the type typically analyzed in accordance with the invention to determine if a prominent wave exists.

The second related waveform trace is analyzed and filtered, if needed, until a primary peak is found. A typical well defined brain stem signal is depicted in FIG. 2. The vertical axis of the graph represents microvolts, while the horizontal axis is a measure of time. The graph of FIG. 2 has vertical graduations of 0.12 microvolts, and horizontal graduations of 1.5 milliseconds. In order to clearly understand the invention, there is illustrated typical brain stem waveform traces 27 and 29, with Wave V identified as reference characters 31 and 33. Traces 27 and 29 are related, in that one such waveform trace 27 is obtained as a result of the averaging of a number of responses to an auditory stimulus during a first test. A second substantially identical test is then conducted, generally a short time later, to obtain an averaged sum of responses for the second waveform trace 29.

Figure 3:
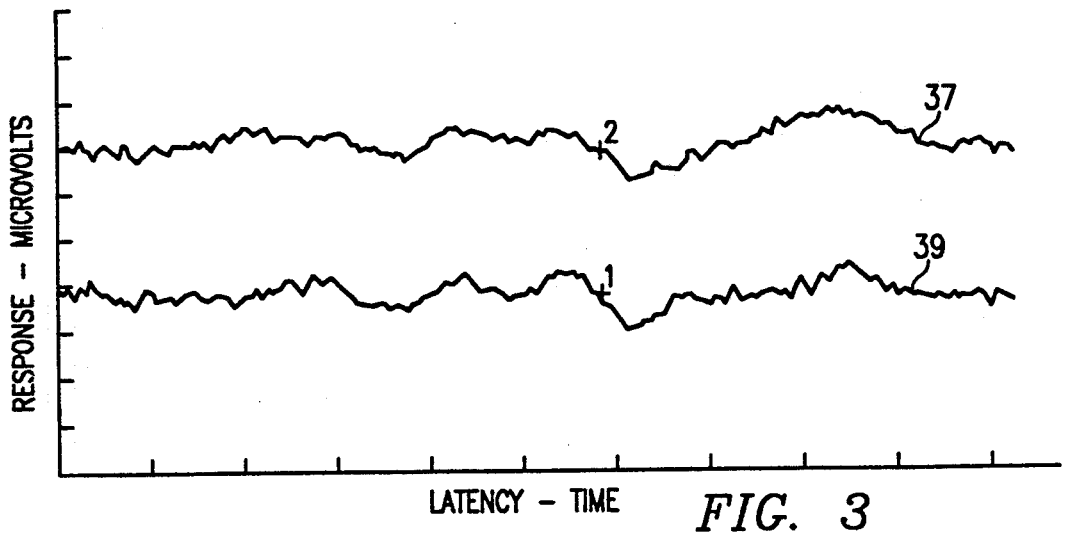

The cursor mark 28 on each of the waveform traces 27 and 29 indicates the Wave V latency point selected by the program. A numerical printout 35 presents a visual indication of the calculated latency of Wave V of both traces 27 and 29. For purposes of comparison and appreciation of the invention, FIG. 3 illustrates a pair of traces 37 and 39 which are less defined and much more difficult to analyze. In this instance, the program would generally make many more hierarchial criteria decisions before Wave V could be identified and the associated latency point identified on each of the traces. The following paragraphs discuss in more detail the hierarchial analysis of the computer program of the invention.

Figure 4:
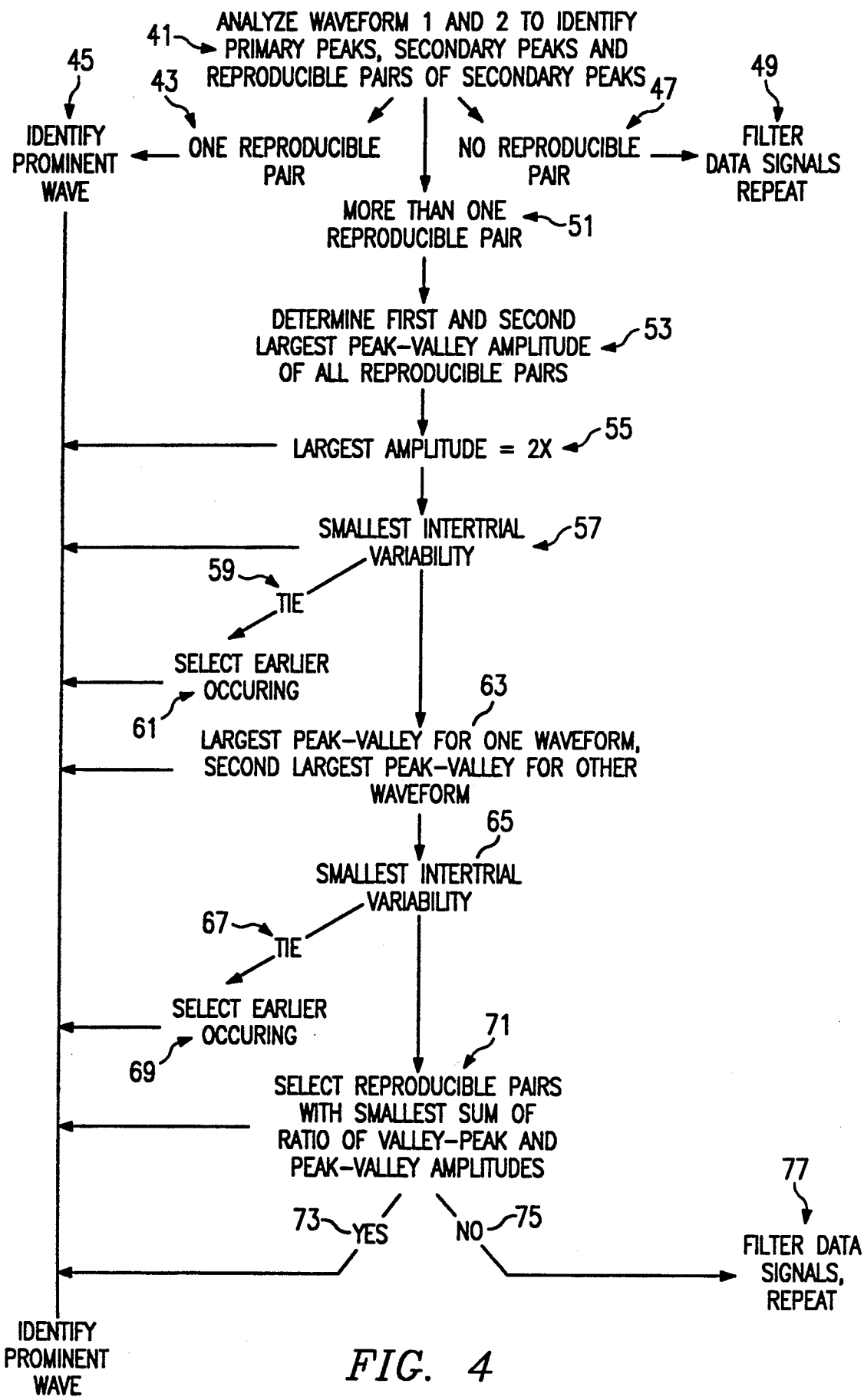
FIG. 4 is a flow chart illustrating the hierarchial level of waveform analysis which is employed for finding and identifying a prominent wave.

The hierarchial structure of the waveform analysis technique of the invention is illustrated in FIG. 4. In block 41, waveform traces 1 and 2 are analyzed to identify primary peaks, secondary peaks, and reproducible pairs of secondary peaks. As used herein, a reproducible wave pair signifies the close correspondence in time of a secondary peak of waveform 1 with a secondary peak of waveform 2. If only a single reproducible pair 43 is found between waveform 1 and 2, a prominent wave is thereby identified 45. If, on the other hand, no reproducible wave pairs are found 47 in either one or the other of the waveform traces, such waveform is again filtered according to a predetermined bandpass 49, whereupon the filtered digital signals are again analyzed for primary peaks. In the event that more than one reproducible wave is obtained between a primary peak of the first and second waveform traces, then the analyzation technique of the invention proceeds according to a hierarchy of analyses and decisions to determine whether or not a prominent wave exists. The first hierarchial level 53 involves the determination of the peak to valley amplitude of reproducible secondary peaks, and a comparison of the amplitudes thereof to determine reproducible peaks having a largest amplitude, and associated reproducible peaks having a second largest amplitude. If such a largest peak-valley amplitude of a reproducible pair is found, analysis is continued 55 to determine if the amplitudes differ by a factor of 2X. If so, the largest amplitude reproducible pair is identified as the prominent wave. If, on the other hand, such a 2X amplitude relationship does not exist, the reproducible pairs are analyzed, and the pair with the smallest intertrial variability 57 is selected and identified as the prominent wave. In the event of a tie 59, that being where the reproducible pairs have substantial equal intertrial variabilities, the reproducible pair of secondary peaks occurring earlier 61 in the sequence is selected and identified as the prominent wave.

Again, in the event that no reproducible waves correspond to the foregoing, the waveform traces 1 and 2 are analyzed 63 to determine as to reproducible wave pairs in which one has a largest peak-valley amplitude and the other has a second largest peak-valley amplitude. If so, such pair is identified as the prominent wave. If such a largest, second largest amplitude criterion is not satisfied, then a reproducible wave pair is selected having the smallest intertrial variability 65. Also, in the event of a tie 67, the earlier occurring reproducible wave pair 69 is identified as the prominent wave.

Lastly, the hierarchy for identifying prominent waves involves the further analyzation 71 of reproducible waves and the corresponding selection of the wave pairs with the smallest sum of ratios of valley-peak amplitudes and peak-valley amplitudes. If such a wave pair is found 73, it is identified as a prominent wave. If no such wave pair is found 75, the data signals are filtered 77 according to a predetermined bandpass, whereupon the entire procedure of FIG. 4 is again repeated in an attempt to identify a prominent wave. As can be appreciated from the foregoing, the hierarchy noted in FIG. 4 can be utilized for analyzing many waveform types, other than those resulting from brain stem responses, and even in other fields unrelated to the medical sciences. In addition, those skilled in the art being apprised of the foregoing can readily adapt the hierarchy to provide a hierarchial analysis for a single waveform.

With reference now to FIGS. 5a–5g, there are illustrated the detailed steps defining program instructions carried out by the computer 21 for processing signal waveforms and identifying prominent waves. The program or routine of the invention is entered 81 by appropriate action of the computer operator or clinician, such as by manipulating the controls of the computer 21 or associated keyboard (not shown). One of the waveform traces is selected 83 for analyzing the digital signals representative of the analog waveform trace, such as received by the electrodes 11-15 as electrical brain stem signals. In the example, waveform trace 29 is selected to be analyzed first. As noted above, the signals received from the electrodes are differential in nature. Also as noted, a composite signal is formed, resulting from the summation of a number of stimulus-response tests. When analyzing the brain stem response for Wave V, the program establishes 85 a latency of about 5.2-10.5 milliseconds as a time period in which it is expected to identify Wave V. In other words, Wave V is expected to appear, if at all, between 5.2 and 10.5 milliseconds after the click stimulus has been applied to the aural organs of the patient. Other latency periods may be established when analyzing other waveforms for a different type of prominent wave. In addition, the program of the invention may be easily modified so as to be interactive with the operator, in that the operator can input different parameter values to further refine the analyzation and identification of different waves.

In analyzing the differential data during this latency time period, such data is analyzed for a positive slope which is greater than ten arbitrary vertical amplitude units. The units selected for measuring the vertical amplitude of each data sample depend on the equipment employed, and thus may vary. However, it is important that the positive slope be somewhat significant, i.e., greater than about 30°, and not a gradual slope. The program identifies the point on the waveform trace 29 where the slope becomes greater than ten units, whereupon this point is labeled as a preceding trough 87, as shown in FIG. 2, as well as noted in program flow block 89. Next, the program analyzes the sequential digital signals from the preceding trough 87 for identifying a point where the slope of the signal waveform becomes zero or negative. The point at which the slope of the signal waveform 29 becomes zero or negative must occur within a certain time period after the preceding trough 87, generally about two milliseconds. The zero or negative slope point in FIG. 2 is defined as the primary peak 88. The program continues analyzing 97 the digital signals of the waveform 29 subsequent to the primary peak 88 to find a positive slope which is again greater than 10 vertical units. If a positive slope greater than 10 units is not found in a 0.9 millisecond interval after the primary peak 88, the program defines the 0.9 millisecond point as a succeeding trough. This aspect, shown in program flow block 101, detects gradual slopes which otherwise would not lead to a real succeeding trough within the 5.2-10.5 millisecond latency period. If on the other hand, the program identifies a slope greater than 10 vertical units, such point is defined as a succeeding slope. In FIG. 2 such a point is shown as reference character 98. After identifying the preceding trough 87, the primary peak 88 and the succeeding trough 98, the amplitude characteristics thereof are analyzed. Particularly, the program calculates 103 the peak to trough amplitude between the primary peak 88 and succeeding trough 98. If this amplitude is greater than about 0.06 microvolts, the digital signals of the waveform trace 29 between the preceding trough 87 and succeeding trough 98 are defined as a bona fide primary peak or a real wave. If the amplitude is less than about 0.06 microvolts, then the data between such points is not considered a bona fide primary peak.

The foregoing analysis continues throughout the predefined latency period to define other primary peaks. In the event a primary peak is not identified in the latency period, the program commences a filter sequence 104. According to the filtering route, the digital signals of the selected waveform trace 29 are filtered to remove a high frequency content of the waveform. Such digital filtering routines are conventionally available for filtering digitized waveforms according to selected bandpasses. FIG. 5g illustrates a filter sequence or schedule through which the program sequences in an attempt to find a primary peak in the selected waveform trace. In other words, in a first pass of analyzing the digital signals, if a primary peak was not found, then the first filter sequence with a bandpass of 1-8000 Hz is carried out. After the first filter sequence, the filtered digital signals are analyzed according to program flow blocks 83-103. Again, if no bona fide primary peak is found, the second filter sequence is carried out, the filtered digital signals are analyzed, and so on, until a bona fide primary peak is found. If the filter sequence of all bandpasses is exhausted and yet no bona fide primary peak is found, then no prominent wave can be found, whereupon such status is presented by the computer 21 on the visual display 23.

Assuming a bona fide primary peak is eventually found, the program returns 105 to the original unfiltered raw digital signals (FIG. 5b) and examines each data point from the primary peak 88 to succeeding trough 98 to define secondary peaks, if any exist. The program examines pairs of odd digital signals, and pairs of even digital signals and compares the amplitude characteristics of each in the following manner: $(X+2)-x$, $(X+4)-(X+2)$, . . . , and $(X+3)-(X+1)$, $(X+5)-(X+3)$, . . . etc., where x is each digital signal of the sequence of digital signals of the waveform trace 29. This is shown as blocks 111 and 113. If the amplitude difference between the pairs of digital signals examined is greater than $-20$ vertical units, the program registers this as a possible secondary peak.

Figures 6A, 6B:
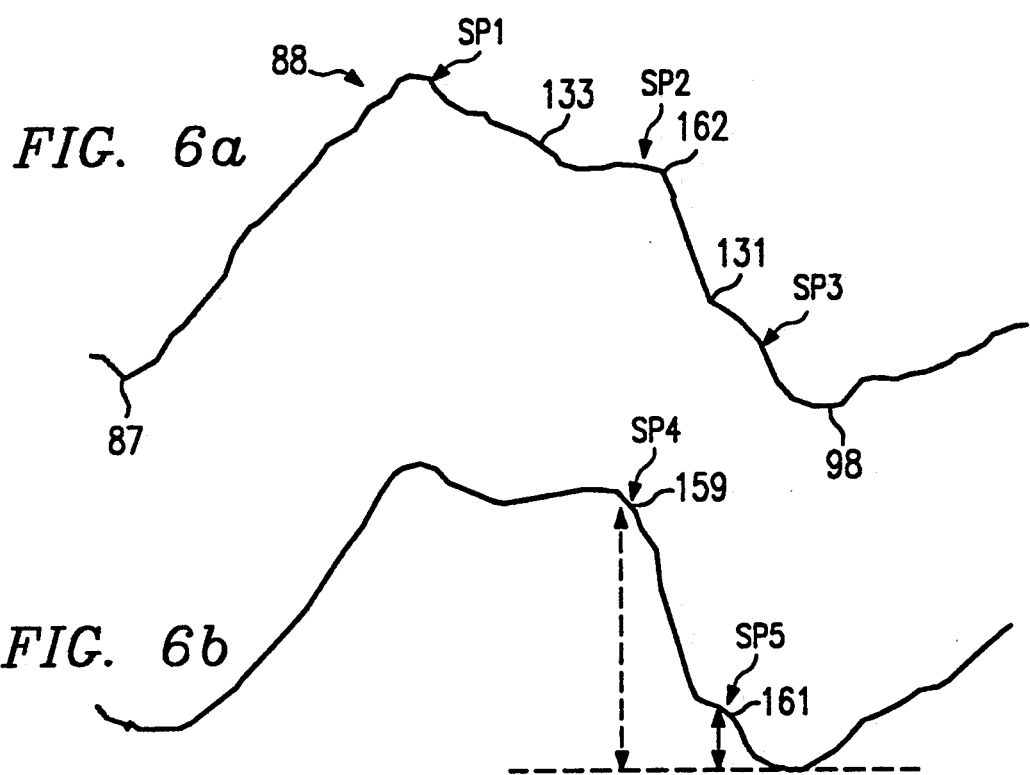
FIG. 6a and 6b are portions of respective waveforms illustrating the various characteristics which undergo analysis according to the invention to determine secondary peaks.

FIG. 6a illustrates three points which are identified by the program of the invention as satisfying this criteria. The three points are labeled as secondary peak SP1, SP2 and SP3. The program then analyzes each one of these secondary peaks to find a location on the bona fide primary peak 88 which can be identified as the prominent wave, e.g., Wave V. The amplitude from each secondary peak to the succeeding trough 98 is calculated 117, as is the amplitude from the primary peak 88 to the succeeding trough 98. If the amplitude characteristic of each secondary peak is at least 60% the amplitude of the primary peak 88, then the secondary peak is retained as a candidate for a Wave V (block 125). In practice, an experienced clinician would conclude that such secondary peaks are possible candidates as a Wave V latency point.

Figure 5A:
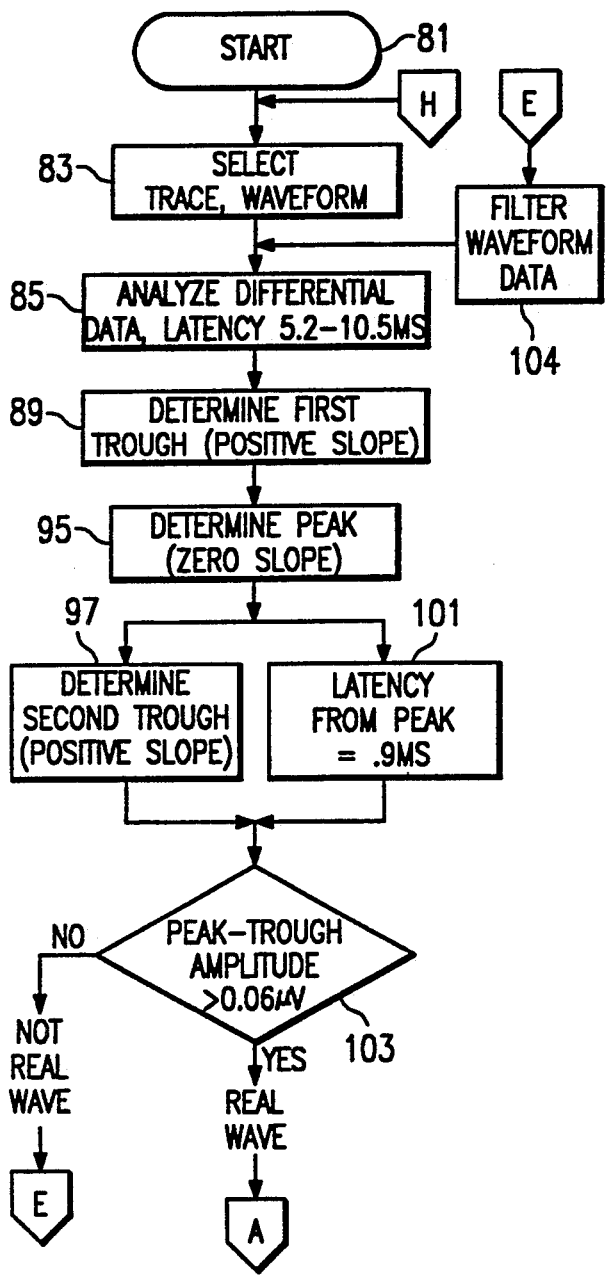
FIGS. 5a-5g are flow charts illustrating the detailed computerized analysis which digitized waveforms undergo to ascertain whether or not a prominent wave exists.
Figure 5B:
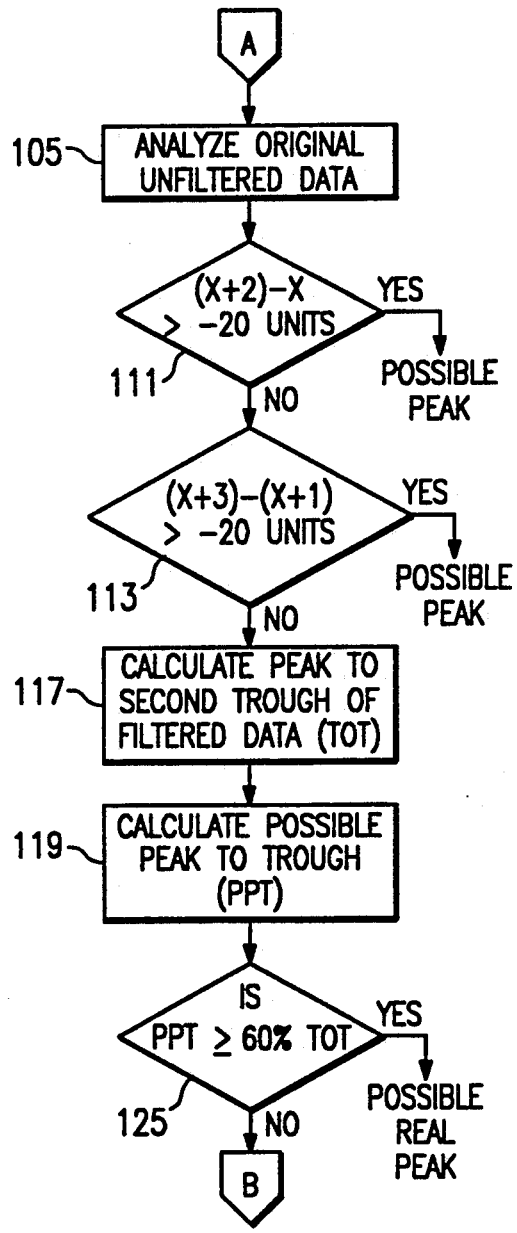
Figures 5C, 5D:
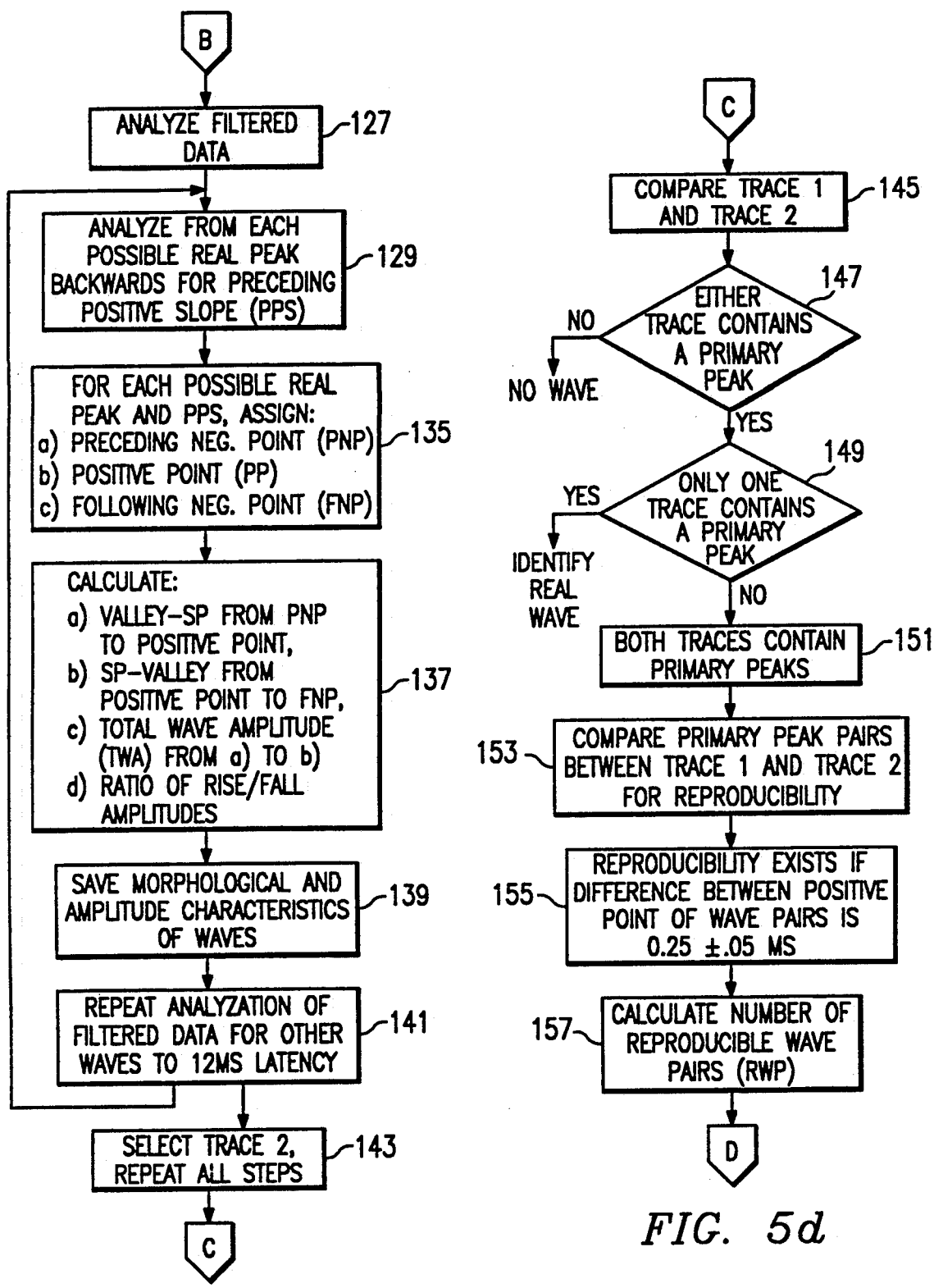

Continuing with the waveform analyzation of the invention, and as shown in FIG. 5c, filtered waveform digital signals of the primary peak 88 are analyzed 127 to ascertain particular characteristics of the secondary peaks SP2 and SP3. If no filtering is necessary to initially determine the primary peaks and associated secondary peaks, then such unfiltered digital signals are analyzed. In any event, the digital signals of each secondary peak, for example SP3, are analyzed backwards toward the primary peak 88 to determine the first positive slope which is greater than ten vertical units. This is illustrated in program flow block 129. For secondary peak SP3, such a positive slope would be identified at the location indicated by reference character 131. In like manner, another preceding positive slope (PPS) is indicated at location 133. This examination continues until all preceding positive slopes of the secondary peaks are identified. In addition, the digital signals of the primary peak are analyzed to find a preceding negative point or slope (PNP) greater than ten vertical units associated with each secondary peak SP2 and SP3. In the example, a preceding negative point, common to both secondary peaks SP2 and SP3, is identified at the primary peak 88 as the amplitude of the digital signals decrease in the direction of the preceding trough 91.

Also, according to program flow block 135, the digital signals are analyzed to determine a positive point for each secondary peak, as well as a following negative point (FNP). As noted above, the positive points of each secondary peak SP2 and SP3 are found by determining the largest amplitude digital signal associated with each such secondary peak. The following negative point of each secondary peak is determined by analyzing the digital signals subsequent thereto until a positive slope greater than ten vertical units is found. In the example, the succeeding trough 98 corresponds to the following negative point. Also, the following negative point is common to both secondary peaks SP2 and SP3 as no other positive slopes of ten vertical units exist between the primary peak 88 and the succeeding trough 98. The points preceding and succeeding each secondary peak are similar to preceding and succeeding valleys.

According to the program flow block 137, the digital signals of the primary peak 88 are further analyzed to develop amplitude characteristics of the secondary peaks SP2 and SP3. For example, a preceding negative point to each secondary peak positive point is determined, as well as a positive point to a following negative peak amplitude. With this amplitude data, a total wave amplitude (TWA) is calculated by a summation of elements (a) and (b) of program flow block 137. In addition, a ratio is calculated using the rise to fall amplitudes of each secondary peak, defined by the division of the valley-peak amplitude divided by the peak-valley amplitude of each secondary peak SP2 and SP3. This information is stored for possible later use in determining whether or not a prominent wave exists. The amplitude characteristics developed according to program flow block 137 defines the morphological and amplitude characteristics 139 of the secondary peaks of the waveform trace.

As shown in program flow block 141, the foregoing data signal analyzation is carried out in a similar manner for the remaining digital signals of the waveform subsequent to the succeeding trough 98 identified above. The process is repeated to determine subsequent primary peaks, if any, and associated secondary peaks, until the latency time of about 10.5 milliseconds is reached, whereupon analyzation of the data signals is halted. In other applications where significant signals are expected to be found after such period of time, it is understood that further analyzation of digital signals would be carried out.

According to the invention, and as indicated in program flow block 143, the second waveform trace 27 is analyzed in a substantially identical manner as described above in connection with the program flow blocks 129-141. In essence, all primary peaks, associated secondary peaks and amplitude characteristics are determined for the second waveform trace 27. Again, filtering sequences are employed, if needed, in order to define primary peaks satisfying the criteria set forth above. As will be noted in detail below, the amplitude characteristics associated with the first waveform trace 29 are compared with those of the second waveform trace 27 to determine reproducibility and to identify a latency point which uniquely identifies a prominent wave, and in the present example, Wave V.

With reference now to FIG. 5d, program flow block 145 depicts the commencement of the comparison of digital signals between the first waveform trace 29 and the second waveform trace 27. First, the data gathered which characterizes each waveform trace is compared to determine if either trace contains a real wave, as noted by program flow block 147. If one of the waveform traces contains no bona fide primary peak, then a final conclusion is available, in which no prominent wave can be found according to the technique of the invention. If both waveform traces contain a primary peak, and only one primary peak each, then a conclusion can be readily achieved in which a prominent wave is identified. This is illustrated in program flow block 149 on an affirmative decision of such block. On a negative decision, meaning that one or both waveform traces contain more than one bona fide primary peak, then further analyzation 151 must be carried out to select, based upon a hierarchy of decision levels, which primary peak corresponds to the prominent wave.

As shown in program flow block 153, the digital signals of the first waveform trace 29 and the second waveform trace 27 are analyzed and compared to determine reproducible characteristics therebetween. As noted above, reproducibility means the time-wise correspondence between characteristics of one waveform trace and the same characteristics of the second waveform trace. Specifically, the waveform characteristic which is analyzed for time correspondence is the positive point of the secondary peaks SP2 and SP3. According to the preferred form of the invention, when analyzing brain stem waves, reproducibility is found if the positive points of corresponding secondary peaks of the first waveform trace 29 and the second waveform trace 27 are within about 0.25 milliseconds. This is noted at program flow block 155.

In carrying out the steps for determining reproducibility of waveform characteristics between the first and second waveform traces, each positive point (PP) of a secondary peak is compared, time-wise, with the positive point of all the other secondary peaks of the other waveform trace. Program flow block 157 illustrates this step. Moreover, and as illustrated in FIG. 6b, there is shown a situation in which a secondary peak SP2 the first trace (FIG. 6a) defines a reproducible waveform with secondary peaks SP4 and SP5 of the second waveform trace (FIG. 6b). The reproducible pairs SP2, SP4 and SP3, SP5 arise in that the positive points 159 and 161 are each within 0.25 milliseconds of the positive point 162 of the first trace.

Figures 5E, 5F:
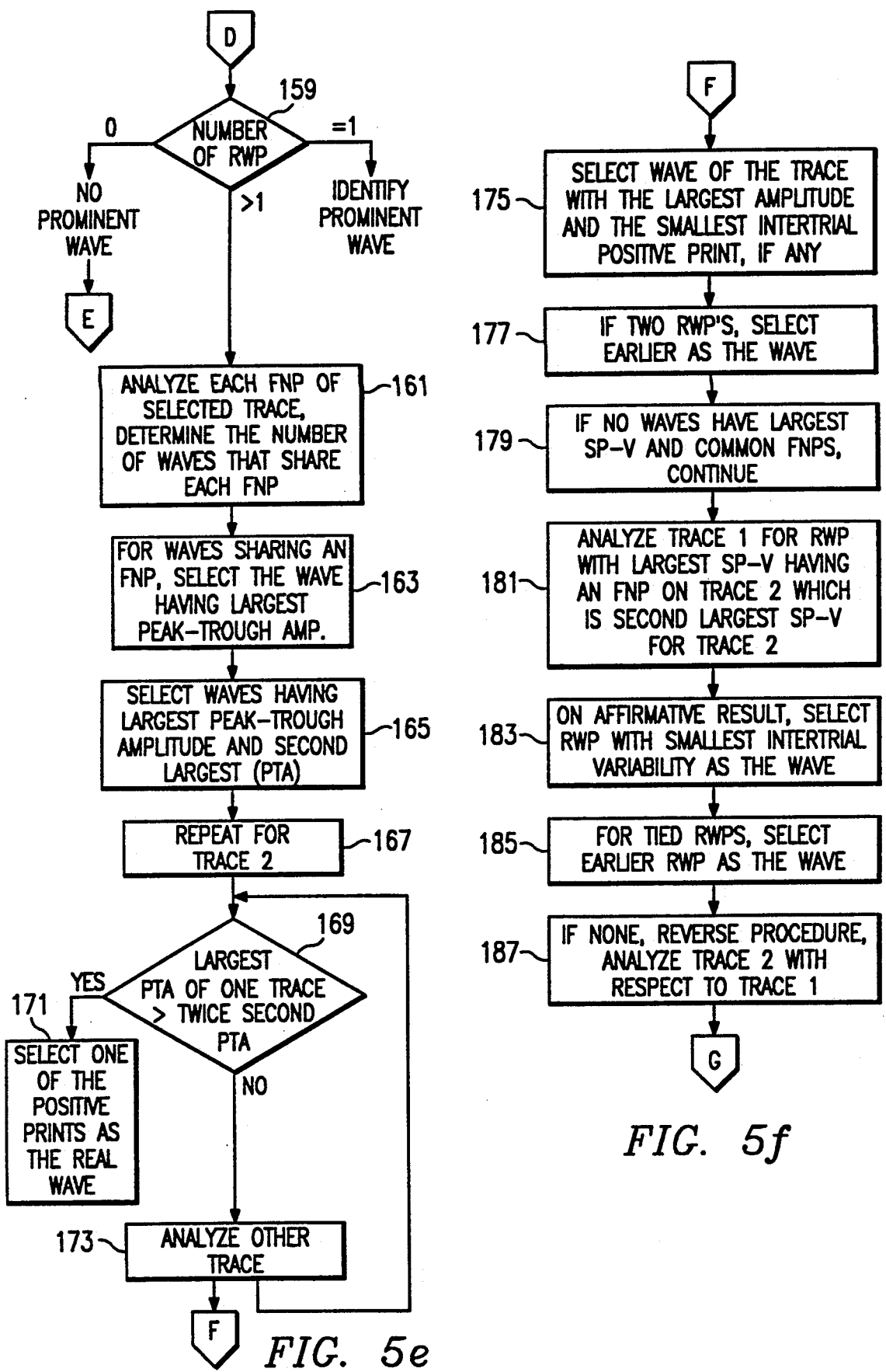
Figures 5G, 7:
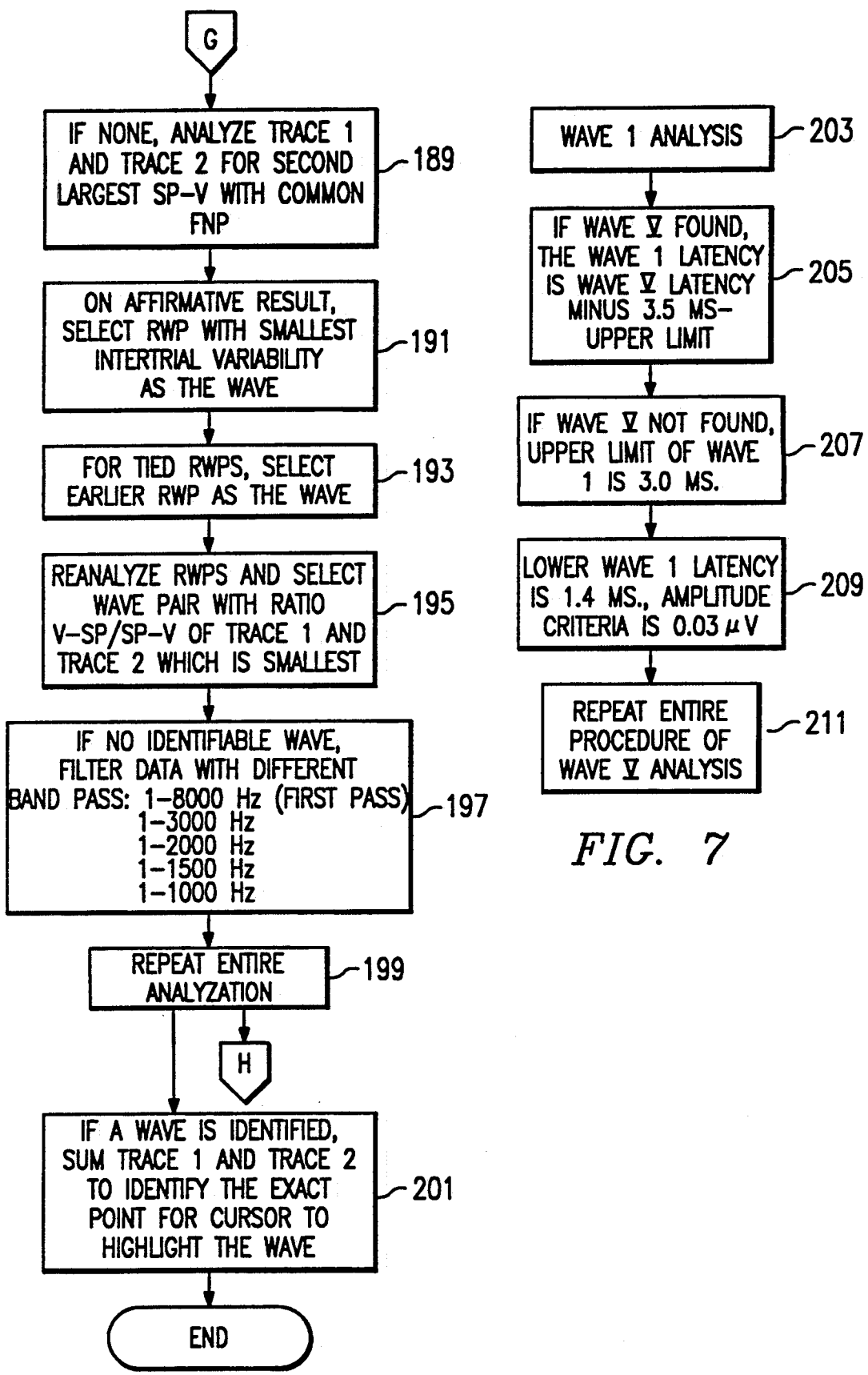
FIG. 7 is a flow chart depicting the basic steps in identifying Wave I of a brain stem electrical signal.

From program flow block 157, processing continues with the instructions corresponding to block 159 of FIG. 5e where the number of reproducible wave pairs (RWP) of secondary peaks is analyzed. If there are no reproducible pairs of secondary peaks between the first waveform trace 29 and the second waveform trace 27, no prominent wave is identified. In this event, the data is filtered and reanalyzed according to branch E. On the other hand, if a single reproducible secondary peak is found between the first and second traces, the latency point associated therewith uniquely identifies the prominent wave. In the event that more than one reproducible wave pair exists, the program flow branches to block 161.

The next hierarchial level involves resolving which secondary peak defines the prominent wave latency point. Each following negative point is recalled from the computer memory, as was calculated and defined according to program flow block 135, to determine the number of secondary peaks which share a single following negative point. It is to be understood that two or more secondary peaks can have a common following negative point, as shown in FIG. 6a, where secondary peaks SP2 and SP3 share the same following negative peak 98. For each secondary peak having a common following negative point, the secondary peak with a largest peak-trough amplitude is selected, as shown in program flow blocks 163 and 165. In addition, this process is repeated for each secondary peak having a second largest amplitude with respect to the common following negative point. Such amplitude characteristic data is calculated, and repeated for trace 2, carrying out the steps of program flow blocks 161-165. The analyzation of trace 2 is noted in program flow block 167.

The next hierarchial level in identifying a prominent wave is to analyze the first trace 29 for reproducible secondary peaks having the largest peak to valley amplitude and the next largest peak to valley amplitude. The program then determines if the largest amplitude is more than twice the next largest amplitude of the associated secondary peaks. In FIG. 6b the peak to valley amplitude of the secondary peak SP4 is more than twice that of the secondary peak SP5, and thus the secondary peak SP4 is deemed to be the reproducible pair associated with the secondary peak SP2 of the first trace. On the other hand, if the 2X factor between the amplitudes is not satisfied, program flow branches to block 173, wherein the other trace is analyzed in the same manner.

If the foregoing yet fails to identify a prominent wave, then the next hierarchial level 175 of FIG. 5f is encountered, in which both waveform traces are analyzed for reproducible pairs having the largest peak to valley amplitudes, as compared with the amplitude characteristics of other reproducible pairs. The reproducible pair having the smallest intertrial variability is selected as the prominent wave, which particularly identifies the latency point thereof. As used herein, the term intertrial variability connotes a time relationship, in which the positive points of the secondary peaks are the most aligned, in time. In the event of a tie, and as noted by program block 177, if two reproducible pairs of secondary peaks have substantially the same intertrial variability, then the one is selected which occurs earlier in time.

According to the next hierarchial level, if no reproducible secondary peak wave pairs have a largest peak to valley amplitude, nor common following negative points (block 179), then the amplitude characteristic data is further compared to determine if there is a reproducible wave pair whose following negative point on the first trace has the largest peak to valley (SP-V) amplitude for that trace, and whose following negative point on the second trace is the second largest peak to valley amplitude for the second trace. This step is depicted as block 181 in FIG. 5f. On an affirmative result of this analysis, the reproducible pair of secondary peaks with the smallest intertrial variability is chosen as the prominent wave. Program flow block 183 illustrates this step. Again, if two reproducible pairs of secondary peaks cannot be resolved, because of a tie, then the earlier occurring in time reproducible wave pair is selected as the prominent wave (block 185). As noted in program flow block 187, if a prominent wave cannot yet be resolved from the foregoing, the same analysis is carried out for program blocks 181-185, but analyzing trace 2 with respect to trace 1.

With regard to FIG. 5g, yet another hierarchial level is encountered in order to identify a prominent wave. This level involves a search of reproducible wave pairs between the first and second waveform traces, for secondary peak wave pairs having a second largest peak to valley amplitude, and with the same following negative point. Program flow block 189 illustrates this hierarchial level. If such a reproducible pair is found, the reproducible wave pair with the smallest intertrial variability is selected as the prominent wave, as shown by program flow block 191. Again, for tied reproducible wave pairs satisfying the criterion of program flow block 191, the earlier occurring reproducible wave pair is selected, as noted by block 193.

Finally, the last hierarchial level is encountered after progressing through the foregoing hierarchial levels. Program flow block 195 illustrates the final hierarchial level, in which all reproducible wave pairs are analyzed, and the pair selected whose sum of ratios, as calculated according to block 137, step d), is the smallest, as between the first and second waveform traces. The reproducible wave pair with the smallest ratio is identified as the latency point for the prominent wave.

As noted throughout the program flow of FIG. 5, when filtering of the digital signals is called for, the first sequence includes a filter bandpass of 1-8,000 Hz. A second pass of the program involving a second filter sequence is carried out using a band pass of 1-3,000 Hz. Subsequent bandpasses of 1-2,000, 1-1,500 and 1-1,000 Hz bandpasses comprise the last sequences of the digital signal filtering according to the invention. Of course, other applications employing the invention may require that other bandpasses and/or sequences be needed to satisfy particular needs. With regard to block 199, after filtering the digital signals according to one of the bandpasses, the entire analyzation process is carried out by reentering program flow block 83 to process the newly filtered data. If at the end of the entire digital signal analyzation process a prominent wave is indeed identified, then the associated latency point calculated according to the foregoing and displayed on the computer's CRT display 23, or on other mediums. In the preferred form of the invention, the latency point is identified numerically, as shown in FIG. 2, by displaying the data corresponding to the time period between the click stimulus and the positive point of the secondary peak selected as the latency point. In the alternative, a cursor can be controlled by the computer to highlight the particular point on both waveform traces which identify the latency points of the prominent wave. Other techniques may be utilized to visually display the prominent wave and its latency point. Such a step is indicated in program flow block 201.

If the entire process is carried out, and all filtering sequences exhausted, and if a prominent wave if not found, then such an indication is displayed on the CRT 23.

FIG. 7 depicts various steps in which different parameters are employed in the foregoing waveform analyzation process for identifying Wave I in a brain stem response. As shown in program flow block 205, if Wave V is found, the data can be analyzed for the identification of Wave I. For ascertaining Wave I, the latency thereof is defined by subtracting 3.5 milliseconds from the Wave V latency. Wave I is thus expected to be found within a time period of 1.4 milliseconds and the lesser of either 3.0 milliseconds or a detected Wave V latency minus 3.5 milliseconds. As noted in block 207, if a Wave V is not found according to the foregoing steps, Wave I may yet be determined, but with an upper latency limit of 3.0 milliseconds. Also, and as noted in block 209, the lower latency limit of Wave I is set at 1.4 milliseconds, with an amplitude criteria of a primary peak being 0.03 microvolts. The same steps and hierarchial levels are utilized in analyzing the digital signals of both waveforms to determine whether or not Wave I exists.

FIG. 8a–8m comprises a listing of the source code defining a computer program for carrying out the steps according to the preferred embodiment of the invention. Depending upon the speed of the processor, the entire analyzation process can be carried out in a very short period of time, thus providing on-line capabilities. Typically, a complete waveform analyzation can be carried out in about 10–12 seconds, thereby providing a clinician a conclusion as to the existence of a prominent wave in a very short period of time. Such a technique is very useful to provide doctors and clinicians brain stem analysis results while in a surgical operating room. Importantly, the prompt and accurate analysis of brain stem responses utilizing the invention lessens the constraints on medical personnel, in that the program provides consistent results and is not subject to fatigue, inaccuracies or subjective decisions, as are medical persons after undergoing many hours of waveform analysis. In addition, the invention provides accurate results as to the existence of prominent waves to support a clinician, and thereby essentially provide second opinions. In practice, it has been found that the results of the analyzation technique of the invention conform very well to the selection of prominent waves by experienced and expert clinicians, and thereby may be relied upon with a high degree of confidence. Educational uses of the invention are apparent.

A technical advantage of this invention is that it provides a high degree of correct identification of latency and threshold for normal and abnormal waveforms, while providing sensitivity and specificity that equals that of the practicing audiologist clinician when both the clinician and the program are judged against expert observers in ABR evaluation. Another technical advantage of this invention is that it provides accuracy irrespective of the patient's age, stimulus intensity or stimulus rate. Another technical advantage of this invention is that it reduces the time needed in routine ABR assessment, both during data collection and subsequently during data interpretation. That is, the program can be used by the clinician during data collection to assure adequate reproducibility between trials prior to cessation of testing. Following assessment, the automated analysis can be completed and the clinician can review the results and counsel the patient promptly. Still another technical advantage of the invention is to provide high speed, consistent and untiring performance in intraoperative monitoring under the supervision of a clinician.

While the foregoing illustrates and discloses the preferred embodiment of the invention with reference to the specific analysis of brain stem waveforms, it is to be understood that many changes in program structure and sequence, and application may be made as a matter of engineering choices without departing from the spirit and scope of the invention, as defined by the appended claims.

What is claimed is:

1. A method for analyzing signal waveform trace data to identify a prominent wave, comprising the steps of:
   analyzing digital signals of related first and second waveform traces to define primary peaks of said first and second waveform traces which satisfy a predetermined criteria, each said primary peak having associated preceding and succeeding troughs;
   if a primary peak is not determined by initial analyzation of said data signals, filtering said digital signals with a predefined bandpass and again analyzing the filtered digital signals until one said primary peak is found in each said trace;
   analyzing said primary peaks to determine secondary peaks;
   analyzing said secondary peaks to characterize said secondary peaks according to predefined criteria;
   determining reproducibility of said secondary peaks between said first and second waveform traces; and
   identifying said prominent wave by employing reproducibility criteria for the secondary peaks of said first and second waveform traces.

2. The method of claim 1, further including analyzing said digital signals between two predefined time periods of said first and second signal waveform traces.

3. The method of claim 2, further including analyzing data between a latency period of about 5.2–10.5 milliseconds for identifying a Wave V of a brain stem signal waveform.

4. The method of claim 1, wherein said primary peak and said preceding and succeeding troughs are determined by analyzing said digital signals for slope characterization as measured over a number of digital signals.

5. The method of claim 1, further including identifying said primary peak when an amplitude characteristic of a brain stem signal waveform exceeds about 0.06 microvolts.

6. The method of claim 1, further including analyzing pairs of alternately arranged digital signals to determine said secondary peaks.

7. The method of claim 6, further including analyzing only a downward slope of a primary peak to a succeeding trough digital signals to define amplitude characteristics of said sample pairs by carrying out a subtraction between said digital signal pairs, and comparing a result thereof with a predefined number.

8. The method of claim 1, further including, for each said secondary peak, analyzing digital signals in a reverse direction from a secondary peak to define a preceding valley associated with said secondary peak.

9. The method of claim 1, further including calculating an amplitude characteristic of each said secondary peak, and defining those secondary peaks whose amplitudes exceed a predetermined amplitude as candidates for identifying said prominent wave.

10. The method of claim 9, further including defining said prominent wave candidates as said secondary peaks with amplitudes exceeding 60% of an associated primary peak amplitude, when analyzing brain stem waveforms.

11. The method of claim 1, further including calculating an amplitude characteristic of each said secondary peak utilizing an amplitude from a peak to an associated succeeding valley.

12. The method of claim 11, further including defining said prominent wave by comparing reproducible secondary peaks having a largest secondary peak to succeeding valley amplitude.

13. The method of claim 1, further including defining said prominent wave by comparing reproducible secondary peaks, one said secondary peak of the reproducible pair having a largest secondary peak to succeeding valley amplitude, and the other secondary peak of the reproducible pair having a second largest secondary peak to succeeding valley amplitude.

14. The method of claim 13, wherein said secondary peak is selected as being reproducible if it has an amplitude at least twice that of the other secondary peak associated with the primary peak.

15. The method of claim 14, further including selecting the earlier occurring of said secondary peaks.

16. The method of claim 1, further including comparing secondary peaks of said first waveform trace with secondary peaks of said second waveform trace to determine reproducibility therebetween, and where a secondary peak of one said waveform trace is reproducible with a pair of secondary peaks of the other waveform trace, selecting the earlier occurring secondary peak of the pair as being reproducible.

17. The method of claim 1, wherein for analyzing brain stem signal waveforms for a prominent wave, said reproducibility comprises a window of about 0.25 milliseconds.

18. The method of claim 1, further including defining a prominent wave if there exists a single pair of reproducible secondary peaks associated with said first and second waveform traces.

19. The method of claim 1, further including comparing amplitudes of reproducible secondary peaks of each waveform trace, and selecting a reproducible secondary peak which has an amplitude more than twice the amplitude of a next highest reproducible secondary peak amplitude.

20. The method of claim 19, further including selecting as said secondary peak of said multiple which is more aligned in time with the secondary peak of the other waveform trace.

21. The method of claim 20, further including selecting the earlier occurring secondary peak of said multiple if both secondary peaks of said multiple are substantially tied as to time alignment with the secondary peak of the other waveform trace.

22. The method of claim 21, further including comparing characteristics of said reproducible secondary peaks, calculating a ratio of preceding valley to secondary peak and secondary peak to succeeding valley of each reproducible secondary peak, and defining said prominent wave as the reproducible pair having a smallest sum of said ratios.

23. The method of claim 1, further including carrying out said steps a first time with data filtered according to a predefined bandpass, and if no prominent wave is found, filtering said data with a narrower bandpass and again carrying out said steps.

24. The method of claim 1, further including identifying Wave V for a brain stem signal waveform, said analyzing being carried out on data having a latency between about 5.2–10.5 milliseconds.

25. The method of claim 1, wherein for identifying Wave I of a brain stem signal waveform, said steps are carried out with a latency having a lower limit of about 1.4 milliseconds, and an upper limit of about 3.0 milliseconds if a Wave V is not found, and an upper limit of the Wave V upper latency limit minus about 3.5 milliseconds.

26. The method of claim 1, further including visually displaying said signal waveform, and locating a cursor adjacent a point on said waveform which is analyzed as being said prominent waveform.

27. The method of claim 1, further including identifying said prominent wave which corresponds to said selected reproducible secondary peaks, visually displaying said first and second waveform traces, and visually displaying a calculated latency of a displayed prominent wave of each said first and second waveform traces.

28. A computerized signal waveform processing system, comprising:
   a filter having a plurality of selectable bandpasses;
   a program controlled processor for storing and processing digital signals corresponding to signal waveform;
   an output device controlled by said processor for displaying results of processed digital signals;
   a program having instructions carried out by said processor for analyzing said digital signals, said program being operative to:
   filter said digital signals according to selected bandpasses;
   analyze said filtered digital signals to define primary peaks of said waveform;
   analyze digital data representative of said primary peaks to determine secondary peaks;
   analyze time and amplitude characteristics of said secondary peaks to define a location on said primary peak for identification thereof; and
   provide an output on said output device for indicating a location on said signal waveform which identifies a prominent wave of said waveform.

29. The computerized equipment of claim 28, further including a software routine for filtering said digital signals according to a predefined bandpass characteristic.

30. The computerized equipment of claim 28, wherein said output identifying said prominent wave comprises a cursor.

31. The computerized equipment of claim 28, wherein said output identifying said prominent wave comprises a numerical readout defining a latency point of said prominent wave.

32. A method for analyzing brain stem waveform traces using a computerized signal waveform processing system so as to identify a prominent wave, comprising the steps of:
   storing and processing digital signals using a program controlled processor;
   displaying the processed digital signals;
   analyzing said digital signals using a program having instructions carried out by said processor, said analyzation including:
   analyzing digital signals of related first and second waveform traces to define primary peaks which satisfy a predetermined criteria, each said primary peak having associated preceding and succeeding troughs;

if a primary peak is not determined by initial analyzation of said digital signals, filtering said digital signals with a predefined bandpass and again analyzing the filtered digital signals until one said primary peak is found in each said waveform trace;

analyzing said primary peaks to determine secondary peaks;

analyzing said secondary peaks to characterize said secondary peaks according to predefined criteria;

determining reproducibility of said secondary peaks between said first and second waveform traces; and identifying said prominent wave by employing reproducibility criteria for the secondary peaks of said first and second waveform traces.

33. The method of claim 32, further including analyzing said digital signals between a latency period of about 5.2-10.5 milliseconds for identifying a Wave V of a brain stem signal waveform.

34. The method of claim 32, further including filtering said digital data when a primary peak is not found, and using an ordered filter sequence of bandpass frequencies of:
 (a) Bandpass 1-8000 Hz
 (b) Bandpass 1-3000 Hz
 (c) Bandpass 1-2000 Hz
 (d) Bandpass 1-1500 Hz
 (e) Bandpass 1-1000 Hz wherein the sequence of bandpasses are used until a primary peak is found.

35. The method of claim 32, further including determining said reproducibility by comparing, time-wise, secondary peaks of the first waveform trace with secondary peaks of the second waveform trace, and selecting a secondary peak on the first waveform trace that is within about 0.25 milliseconds of a secondary peak on the second waveform trace as a reproducible pair.

36. The method of claim 35, wherein for multiple reproducible pairs, further including choosing the reproducible pair that occurs earlier in time as said prominent wave when the reproducibility criteria analysis employed to identify said prominent wave determines that multiple reproducible pairs qualify as a prominent wave.

* * * * *